United States Patent [19]
Blake, III et al.

[11] Patent Number: 5,647,836
[45] Date of Patent: Jul. 15, 1997

[54] METHOD AND MEANS FOR TREATING FEMALE URINARY INCONTINENCE

[76] Inventors: Joseph W. Blake, III, 77 Locust Ave., New Canaan, Conn. 06840; Robert M Spitz, 58 Gallup La., Waterford, Conn. 06385

[21] Appl. No.: 535,654

[22] Filed: Sep. 28, 1995

[51] Int. Cl.$^6$ ............................................. A61F 2/04
[52] U.S. Cl. ............................................. 600/30
[58] Field of Search ............ 600/830, 29; 128/885, 128/DIG. 25; 607/138

[56] References Cited

U.S. PATENT DOCUMENTS

| | | | |
|---|---|---|---|
| 4,139,006 | 2/1979 | Corey | 600/29 |
| 5,007,894 | 4/1991 | Enhorning | 600/29 |
| 5,256,133 | 10/1993 | Spitz | 600/30 |
| 5,417,226 | 5/1995 | Juma | 600/29 |

*Primary Examiner*—Angela D. Sykes
*Attorney, Agent, or Firm*—Patrick J. Walsh

[57] ABSTRACT

A female urinary stress incontinence remedy in which endopelvic fascia attached to either side of the urethra is elevated and held in place by means of a pair of anchors comprised of upper and lower stays interconnected by suture and surgically positioned on either side of the urethra with the upper stay positioned above the rectus fascia and the lower anchor stay engaging the endopelvic fascia, exposed by aligned insisions in the vaginal wall.

10 Claims, 3 Drawing Sheets

METHOD AND MEANS FOR TREATING FEMALE URINARY INCONTINENCE

BACKGROUND OF THE INVENTION

The present invention relates to female urinary stress incontinence and provides a method and means for treatment.

The prior art reveals a variety of methods and devices for treating female urinary incontinence including surgical procedures for implanting corrective devices.

Lemay U.S. Pat. No. 5,013,192 discloses a surgical technique using local anesthesia for burying a pair of implants to the left and right of a median line at the superior border of the symphsis pubis, threading suture from the vagina through each implant and back through the vagina to provide two ends of each suture protruding from the vagina, and tying the first and second ends of the left and right sutures, respectively, to support and constrict the urethra. Lemay discloses a reinforcing element such as a small strip of biologically acceptable cloth (e.g., Dacron) under the tied ends of the sutures. Lemay also discloses the use of a supporting saddle for holding the neck of the urethra in case incontinence reoccurs after a first procedure. A problem with Lemay is that the lower implant platform may, in time, damage the urethra causing other problems.

Robertson U.S. Pat. No. 5,019,032 improves the Gittes and Loughlin pubovaginal suspension technique for treating incontinence by means of installing sutures between the rectus fascia and vagina. Robertson is primarily concerned with proper placement of the sutures and particularly avoiding the bladder and urethra.

Petros U.S. Pat. No. 5,112,344 discloses a method for treating female incontinence in which a filament is looped between the wall of the vagina and the rectus abdominis sheath in the anterior wall of the abdomen passing to each side of the urethra, and the filament is tightened to bring the vaginal wall and urethra into correct spatial relationship with respect to the pubis so that scar tissue develops between the vaginal wall and the anterior wall of the abdomen. The filament is removed after scar tissue develops. The scar tissue provides a ligament-like interconnection between the vaginal wall and the muscle tissue at the anterior surface of the abdomen.

Annis et al U.S. Pat. No. 4,857,041 discloses a prosthetic device for female incontenence in the form of a cuff around the urethra positioned by sutures attached to the rectus sheath.

Trick et al U.S. Pat. No. 5,114,398 discloses a valve structure placed in the bladder and urethra for treating female incontinence.

Haber U.S. Pat. No. 5,064,434 discloses an implant inserted hypodermically in the vicinity of the urethra to increase local tissue volume in order to control incontinence.

Fernandez et al discloses an artificial sphincter in the form of a magnetic implant for female incontinence.

Hodgson U.S. Pat. No. 4,556,050 discloses an artificial sphincter implant for incontinence using a shape memory member fabricated of NiTinol. The shape memory member has a memory configuration to which the member recovers when heated to recovery temperatures.

In addition to the above patented solutions, there are several common needle suspension procedures for treating stress incontinence including modified Pereyra in which suture interconnects subcutaneous tissue above the rectus fascia to tissue on both sides of the urethra; Raz in which suture interconnects subcutaneous tissue above the rectus fascia to the vaginal wall on both sides of the urethra; and Stamey in which suture interconnects subcutaneous tissue above the rectus fascia to Dacron sleeves located in tissue on both sides of the urethra.

The foregoing patent disclosures and common surgical procedures propose a variety of solutions to the matter of female urinary stress incontinence, nonetheless, none of these disclosures reveal a solution of general application and the challenge is to find simpler ways to correct it.

SUMMARY OF THE INVENTION

The present invention comprises a method and means for treating female urinary stress incontinence performed in an office procedure with local anesthesia without any external incision and with the procedure applied vaginally by needle.

In accordance with the invention, a pair of incisions are made in the vaginal wall on the right and left sides of and parallel to the urethra.

Next, a pair of upper supporting anchor stays each carrying a depending suture are positioned in subcutaneous tissue immediately above the rectus fascia on either side of the urethra. Each upper anchor stay is placed by means of a needle or cannula applied through the right and left incisions in the vaginal wall, and through the rectus muscle and rectus fascia. The skin is not pierced. The depending suture of each upper anchor stay extends downwardly through its respective incision in the vaginal wall.

A lower anchor stay is fitted onto each suture and is drawn upward into vaginal incisions to elevate the endopelvic fascia on either side of the attached urethra. Thereafter, when desired tension has been attained, each stay is crimped to secure it in place and the suture ends below the lower stays are snipped.

OBJECTS OF THE INVENTION

It is an object of the invention to provide a minimally invasive remedy for female urinary stress incontinence applied vaginally in an office procedure, with local anesthesia, and without piercing the abdominal wall.

It is an object of the invention to provide a female incontinence remedy in which endopelvic fascia attached to either side of the urethra is elevated and held in place by means of a pair of anchors comprised of upper and lower stays interconnected by suture and surgically positioned on either side of the urethra with the upper stay positioned above the rectus fascia and the lower anchor stay engaging the endopelvic fascia, exposed by aligned insisions in the vaginal wall.

It is a further object of the invention to provide for positioning of the two anchors, each with upper and lower stays and interconnecting suture, by means of a cannula inserted through aligned incisions in the vaginal wall on either side of and parallel to the urethra, and through rectus muscle and rectus fascia for locating the upper stays above the rectus fascia and the lower clips in the endopelvic fascia, exposed by aligned insisions in the vaginal wall.

It is a further object of the invention to provide a stay and suture arrangement whereby the suture is fastened by deforming the stay.

Other and further objects of the invention will occur to one skilled in the art with an understanding of the following detailed description of the invention or upon employment of the invention in practice.

DESCRIPTION OF THE DRAWING

A preferred embodiment of the invention has been chosen for purposes of illustrating the construction and operation of the invention and is shown in the accompanying drawing in which.

DETAILED DESCRIPTION OF THE INVENTION

Figure 1:
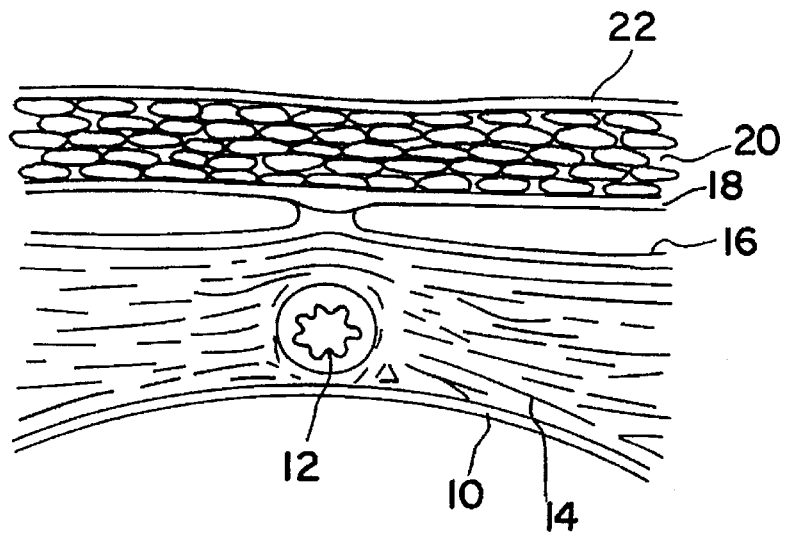
FIG. 1 is a section view showing positions of vaginal wall, urethra, endopelvic fascia, rectus muscle, rectus fascia, subcutaneous tissue and skin.
Figure 2:
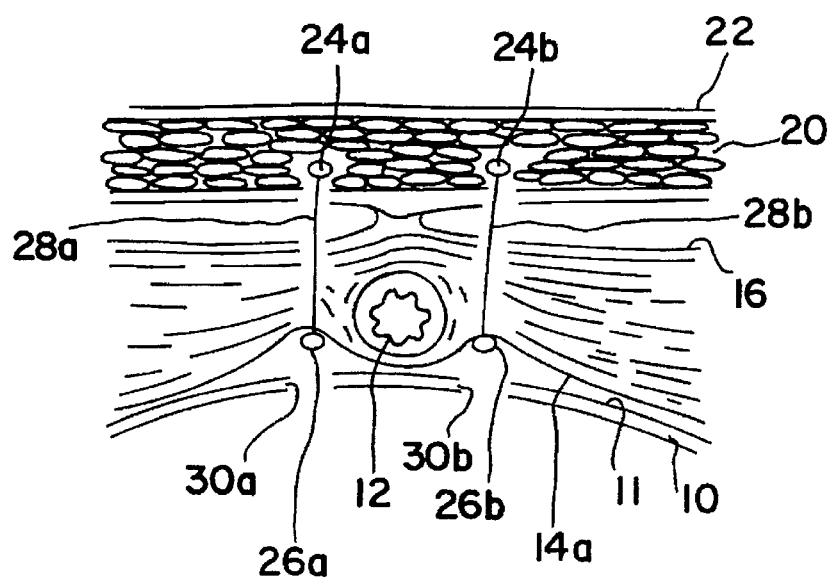
FIG. 2 is a section view corresponding to FIG. 1 after completion of the procedure according to the invention.
Figure 3:
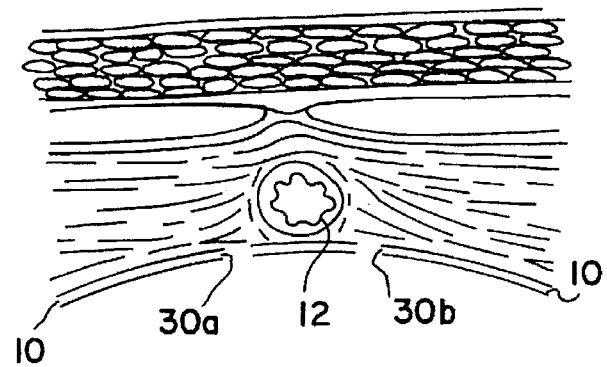
FIGS. 3–6 are section views corresponding to FIG. 1 showing, in sequence, vaginal application of anchor stay and suture by cannula.
Figure 4:
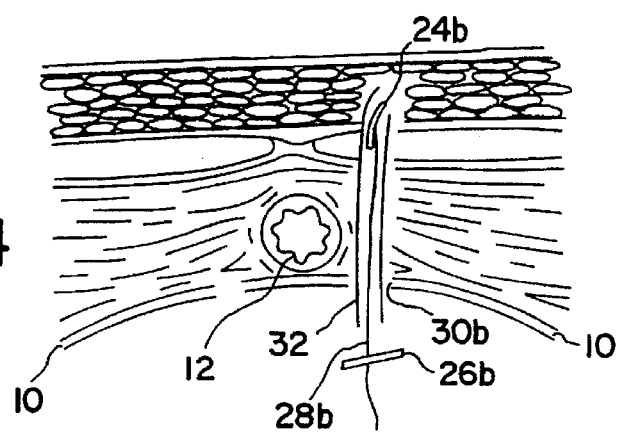

Referring now to FIG. 1, the method and means of the invention are applied to the parts shown in section including vaginal wall 10, urethra 12, endopelvic tissue 14, rectus muscle 16, rectus fascia 18, subcutaneous tissue 20 and skin 22. FIG. 2 illustrates the same section after completion of a preferred procedure of the invention with upper 24a–b and lower 26a–b anchor stays with interconnecting sutures 28a–b acting together to elevate endopelvic tissue in the vicinity of the urethra. In this description, the term "anchor" refers to an assembly of upper and lower stays interconnected by suture.

As shown in FIG. 2, left and right anchors including upper and lower stay pairs are positioned to each side of the urethra with the upper stays 24a–b above the rectus fascia 18 and the lower stays 26a–b embedded between the vaginal mucosa 11 and the underlying endopelvic fascia 14a exposed by aligned incisions 30a–b in the vaginal wall. A suture interconnects the upper and lower stays of each anchor, drawing the stays together so as to elevate the endopelvic fascia and the attached urethra.

The procedure for implanting each anchor is illustrated in sequence in FIGS. 3–6. First, two incisions 30a–b are made in the vaginal wall 10 with one on each side of and parallel to the urethra 12. Each incision is slightly larger than the respective stay 26a–b to be embedded therein in the course of the procedure.

The incisions can be made through the full thickness of the vaginal wall. It is preferable to make each incision penetrate the epithelium, but not the full thickness of the vaginal wall. By restricting each incision to the full thickness of the epithelium, part of the vaginal wall can be used for support of the lower anchor stays.

Next, a cannula 32 is loaded with an anchor including an upper stay 24b affixed to a suture 28b that slidably receives a lower stay 26b through an opening 34 (FIGS. 7–8) in the stay, enters the vagina and pierces the endopelvic fascia 14a exposed by the incision 30b to the one side of the urethra and continues on to pierce the rectus muscle 16 and the rectus fascia 18 above the pubis (not shown).

Figure 5:
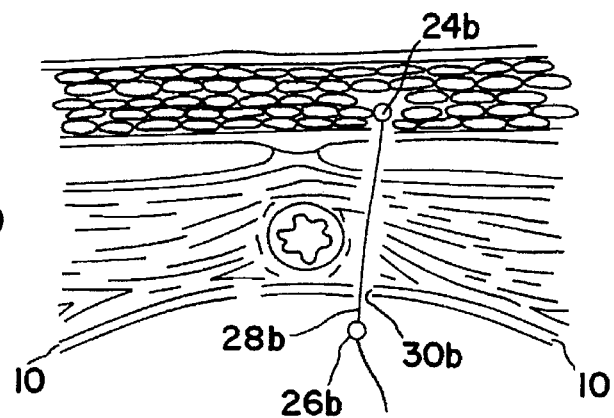
Figure 6:
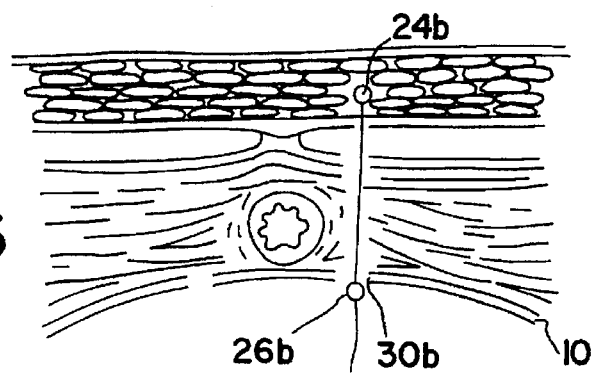

After discharging the upper stay above the rectus fascia, without piercing the skin, the cannula is withdrawn leaving the upper stay in place with the suture extending from the stay through the rectus fascia, rectus muscle, and through the incision in the vaginal wall (FIG. 5). The lower stay is drawn up on the suture to elevate tissue in the vicinity of the urethra. When the correct degree of elevation is achieved (see FIG. 2), the lower stay is secured to the suture as by crimping the stay by a suitable tool 36 (FIGS. 7 and 8) to compress its suture opening 34.

The anchor positioning and securing step is repeated on the other side of the urethra resulting in a double stay and suture implant on both sides of the urethra elevating the endopelvic fascia and the adjacent urethra.

Figure 7:
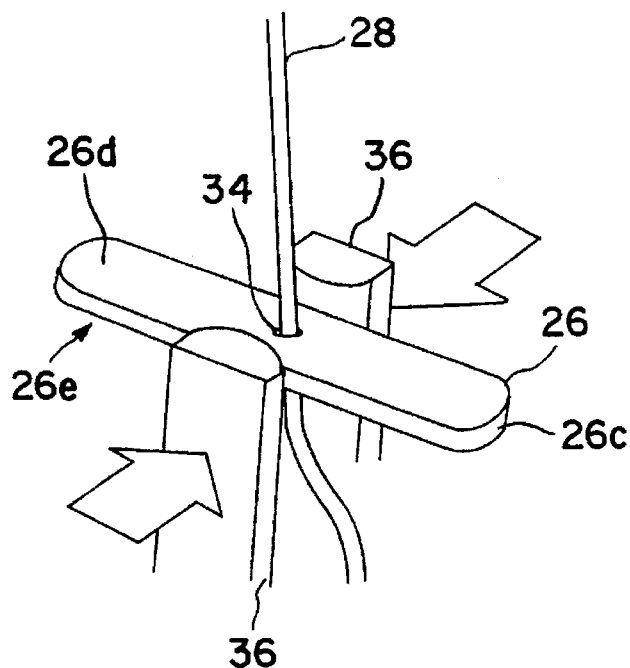
FIGS. 7 and 8 are detail perspective views of the suture and lower stay of an anchor showing a stay being fastened to suture.
Figure 8:
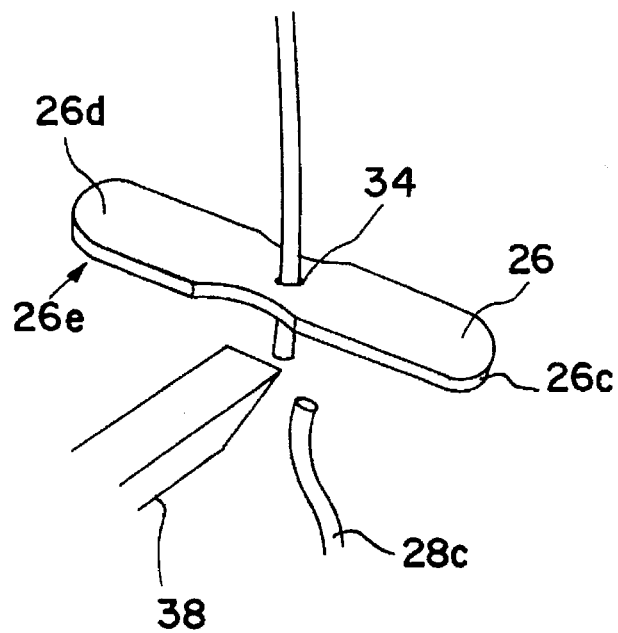

A lower anchor stay 26 is shown in FIGS. 7 and 8 in the form of an elongate plate 26c with flat upper 26d and lower 26e surfaces. A central opening 34 slidably receives suture 28. After the stay is implanted, the tool 36 crimps the stay deforming opening 34 and permanently affixing stay to suture. The lower portion 28c of the suture is snipped away by cutter 38. The upper stay may have the same or similar shape for engaging the rectus fascia.

The suture and upper stay may be unitarily formed of any suitable biologically compatible plastic material such as polypropylene, or may be a combination of a biologically compatible plastic and metal, such as titanium.

I claim:

1. A method of treating female urinary stress incontinence comprising the steps of:

a. making at least two incisions in the vaginal wall with one incision on each side of and parallel to the urethra, with each incision exposing endopelvis fascia, b. assembling at least two anchors with each anchor having an upper stay affixed to a suture and a lower stay having an opening for slidably receiving the suture, c. loading an anchor into a cannula, d. inserting the cannula into the vagina to pierce the endopelvic fascia exposed by the incision to the one side of the urethra and continuing on to pierce the rectus muscle and the rectus fascia above the pubis, e. discharging the upper stay above the rectus fascia, f. withdrawing the cannula leaving the upper stay in place with the suture extending from the stay through the rectus fascia, rectus muscle, and through the incision in the vaginal wall, g. drawing the lower stay up on the suture to elevate tissue in the vicinity of the urethra h. securing the lower stay to the suture when the correct degree of elevation is achieved, and i. repeating steps c through h through the incision on the other side of the urethra.

2. The method of claim 1 in which each incision is restricted to the epithelium of the vaginal wall.

3. A method of treating female urinary stress incontinence comprising the steps of:

a. making two incisions in the vaginal wall with one incision on each side of the urethra, with each incision exposing endopelvic fascia, b. assembling two anchors with each anchor having an upper stay affixed to a suture and a lower stay having an opening for slidably receiving the suture, c. positioning the upper stay above the rectus fascia by insertion through the endopelvic fascia exposed by the incision to the one side of the urethra and continuing on to pierce the rectus muscle and the rectus fascia above the pubis, with the suture extending from the upper stay through the rectus fascia, rectus muscle, and through the incision in the vaginal wall, d. drawing the lower stay up on the suture to elevate tissue in the vicinity of the urethra e. securing the lower stay to the suture when the correct degree of elevation is achieved, and f. repeating steps c through e through the incision on the other side of the urethra.

4. A method of treating female urinary stress incontinence comprising the steps of:

a. making two incisions in the vaginal wall with one incision on each side of the urethra, with each incision restricted to the epithelium of the vaginal wall, b. assembling two anchors with each anchor having an upper stay affixed to a suture and a lower stay having an opening for slidably receiving the suture, c. positioning the upper stay above the rectus fascia by insertion through the incision to the one side of the urethra and continuing on to pierce the rectus muscle and the rectus fascia above the pubis, with the suture extending from the upper stay through the rectus fascia, rectus muscle, and through the incision in the vaginal wall, d. drawing the lower stay up on the suture to elevate tissue in the vicinity of the urethra e. securing the lower stay to the suture when the correct degree of elevation is achieved, and f. repeating steps c through e through the incision on the other side of the urethra.

5. An implant kit for treating female urinary stress incontinence comprising a pair of anchors, each anchor comprising an upper stay affixed to a length of suture, and a lower stay slidably received on the suture through an opening in the lower stay, the lower stay being deformable by crimping in the vicinity of the opening for securement to the suture.

6. A kit as defined in claim 5 in which the stays are formed of biologically compatible plastic.

7. A kit as defined in claim 6 in which the stays are formed of polypropylene.

8. A kit as defined in claim 5 in which the stays are formed of biologically compatible metal.

9. A kit as defined in claim 8 in which the stays are formed of titanium.

10. An implant kit for treating female urinary stress incontinence comprising a pair of anchor assemblies, each anchor assembly comprising an upper stay affixed to a length of suture, and a lower stay slidably received on the suture through an opening in the lower stay, the lower stay being deformable by crimping in the vicinity of the opening for securement to the suture, a cannula for receiving each anchor assembly for implanting each assembly, and a tool for crimping the lower stay for securement to the suture.

* * * * *